United States Patent [19]
Morehead

[11] Patent Number: 5,678,994
[45] Date of Patent: Oct. 21, 1997

[54] FLEXIBLE TOOTH FOR DENTURES

[76] Inventor: Gordon Morehead, 6644 Fisher Rd., Dallas, Tex. 75214

[21] Appl. No.: 397,923

[22] Filed: Mar. 3, 1995

[51] Int. Cl.⁶ ............................................. A61C 13/28
[52] U.S. Cl. ......................................................... 433/169
[58] Field of Search .............................. 433/168.1, 169, 433/202.1, 177

[56] References Cited

U.S. PATENT DOCUMENTS

| | | | |
|---|---|---|---|
| 2,303,874 | 12/1942 | Brown | 433/167 X |
| 2,380,468 | 7/1945 | Saffir | 433/169 |
| 2,743,515 | 6/1956 | Egger | 433/169 |
| 2,746,149 | 5/1956 | Del Papa | 433/169 |
| 3,197,866 | 8/1965 | Barron | 433/169 |
| 3,226,826 | 1/1966 | Town | 433/168.1 |
| 3,826,002 | 7/1974 | Faust et al. | 433/177 |
| 3,958,334 | 5/1976 | Heimansohn | 433/169 |
| 4,014,095 | 3/1977 | Heimansohn | 433/169 |
| 4,215,986 | 8/1980 | Riess | 433/169 |
| 5,227,602 | 7/1993 | Kuhn | 433/167 X |
| 5,492,470 | 2/1996 | Anders | 433/169 |

*Primary Examiner*—Robert P. Swiatek
*Assistant Examiner*—Elizabeth Shaw
*Attorney, Agent, or Firm*—John F. Bryan, Jr.

[57] ABSTRACT

A flexible tooth for mounting in dentures wherein the top of the tooth or crown and base of the tooth are separate parts bonded together by an annular, wedge shaped elastomeric layer. Limited area planar contact between the crown and base along the central axis provides unyielding resistance to biting forces while angular movement within the elastomeric layer allows flexibility of the crown with respect to the base so as to give a user the feeling of a natural tooth.

4 Claims, 2 Drawing Sheets

FLEXIBLE TOOTH FOR DENTURES

FIELD OF THE INVENTION

The present invention relates to the field of dentures and more particularly to flexible teeth for mounting in such dentures.

BACKGROUND AND SUMMARY

Users generally consider artificial dentures as a necessary evil, tolerable only in view of the alternative. The hard shape cooperates unnaturally with the soft tissues of the mouth where periodontal membrane would allow natural teeth a limited range of flexibility. Flexible teeth especially adapted for mounting in dentures have been proposed in earlier disclosures as illustrated by Barron, U.S. Pat. No. 3,197,866 and Egger, U.S. Pat. No. 2,473,515.

Barron, in common with other previous disclosures, places a resilient layer under the top portion of the tooth. Elastomers typically are stronger and less resilient in compression than in shear, and Barron provides a central cavity in the base which he lines with resilient material to carry both lateral displacement forces and biting forces in compression.

Egger had earlier recognized that flexible teeth made a more natural feeling denture and furthermore, that a hard load path for biting forces and strong resistance to lateral forces were also part of this "feel". Egger thus proposed a rolling crown/base interface comprising a conical "pin" having a radiused tip for fitting into a rounded, conical cup in the opposed part. Divergence of the cone angles allows freedom of movement and filling the conical cavity with elastomer bonds the parts together and results in the desired natural feel.

The natural tooth flexes by moving within the periodontal tissue surrounding its roots, so that its effective flexural center is relatively low. In order to provide strong resistance to lateral forces, the rolling interface of Egger dictates the use of a relatively narrow cone angle. If the cup is in the crown, this narrow angle puts the effective flexural center high in the crown. Conversely, with the cup in the base, elastomer is exposed high on the tooth side wall.

The object of the present invention is to provide a flexible tooth structure which carries biting forces through a hard load path and has strong resistance to lateral displacement forces while flexing in a natural feeling manner.

The present invention provides a hard tooth base and crown with matching contact areas located essentially on the vertical axis of the tooth. The contact areas are bounded by diverging conical surfaces and a substantially annular, relatively resilient, wedge shaped intermediate portion is bonded to these diverging surfaces.

The matching contact areas provide a hard load path for biting forces while, even with relatively flat cone angles, the contact area edges and angular boundary surfaces nest together so as to resist lateral displacement.

DESCRIPTION OF THE DRAWINGS

The aforementioned and other objects and features of the invention will be apparent from the following detailed description of specific embodiments thereof, when read in conjunction with the accompanying drawings, in which.

DETAILED DESCRIPTION OF THE DRAWINGS

Figure 1:
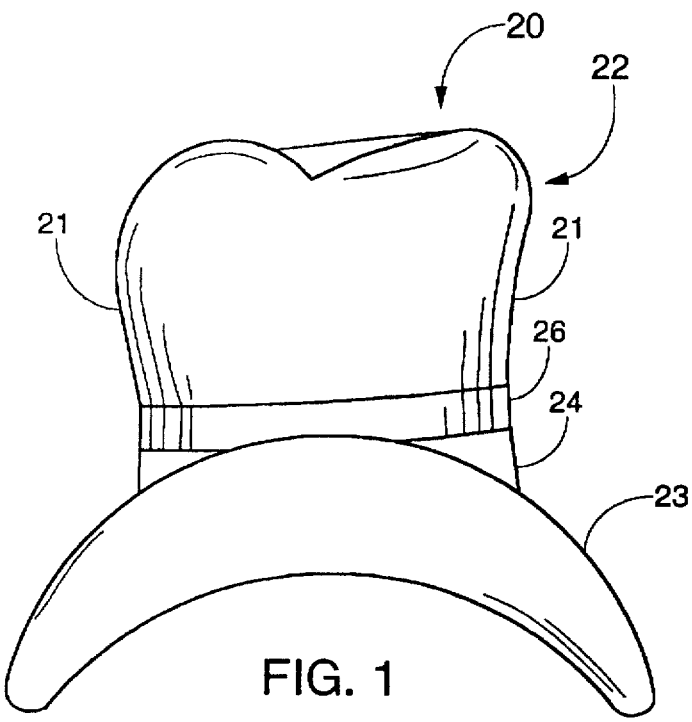
FIG. 1 shows a view of a typical tooth incorporating the present invention.

In FIG. 1, is shown an artificial tooth 20 with side walls 21 mounted in denture 23 and incorporating a preferred embodiment of the present invention. Both crown portion 22 and base portion 24 are molded from an FDA approved thermoplastic or thermosetting material such as an acrylic resin or polyurethane having a final hardness in the range of 75–85 Shore D. Crown portion 22 and base portion 24 are bonded together with a relatively resilient, annular, wedge shaped, intermediate portion 26, which is made of an FDA approved thermosetting urethane such as commercially available MDI resin with 1–4 butanediol hardener. The hardness of intermediate portion 26 which is preferred for a proper degree of resiliency is in the range of 55–65 Shore A. However, according to the preference of the user and the thickness of intermediate portion 26, hardnesses from 20–95 Shore A may be employed.

Figure 2:
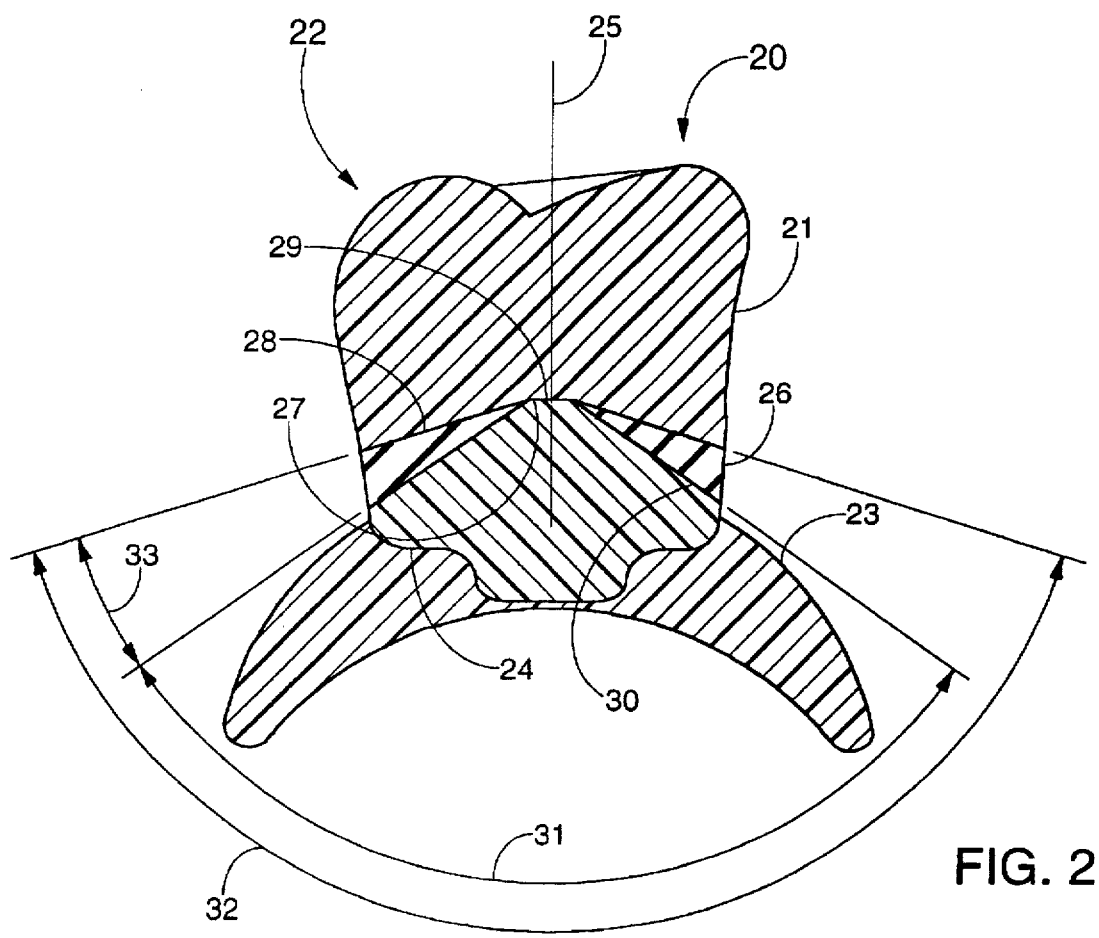
FIG. 2 shows a cross-sectional view of the tooth of FIG. 1.

FIG. 2 shows a cross-section view of the tooth of FIG. 1 seen from the same perspective. Vertical axis 25 is centrally located within the tooth side walls 21 and represents the normal line of action of biting forces imposed on crown 22. Base planar contact area 27 is located along central axis 25 and conical top surface 30 of base 24 extends from the perimeter of contact area 27 downwardly to the tooth side walls 21 at base included angle 31 of 110°. Crown planar contact area 29 abuts directly against base planar contact area 27 so that normal biting forces are carried along a hard, non-resilient load path. Conical crown surface 28 bounds contact area 29, overlying conical base surface 30 at a crown included angle 32 of 130°, and extends to tooth side walls 21. Nesting of the edges of planar base contact area 27 within the angle of conical crown surface 28 resists lateral displacement forces while also allowing flexibility for the crown to realign in response to off-center biting forces. Conical surfaces 28 and 30 are bonded together by resilient intermediate portion 26, the thickness of which is determined by the divergence of the angles 32 and 31 of conical surfaces 28 and 30. These angles 32 and 31 may range from 90° to 160° but the divergence angle 33 should be at least 6° to allow resilient thickness for intermediate portion 26. It should be noted that, in this embodiment, a biting force on crown 22 which is off-center to the left of central axis 25 and which would tend to displace crown 22 to the right, urges the edge of base planar contact area 27 against the boundary line of conical crown surface 28 so as to resist any rightward movement of crown 22. Thus, a relatively flat angle of conical crown surface 28 will resist lateral displacement.

Figure 3:
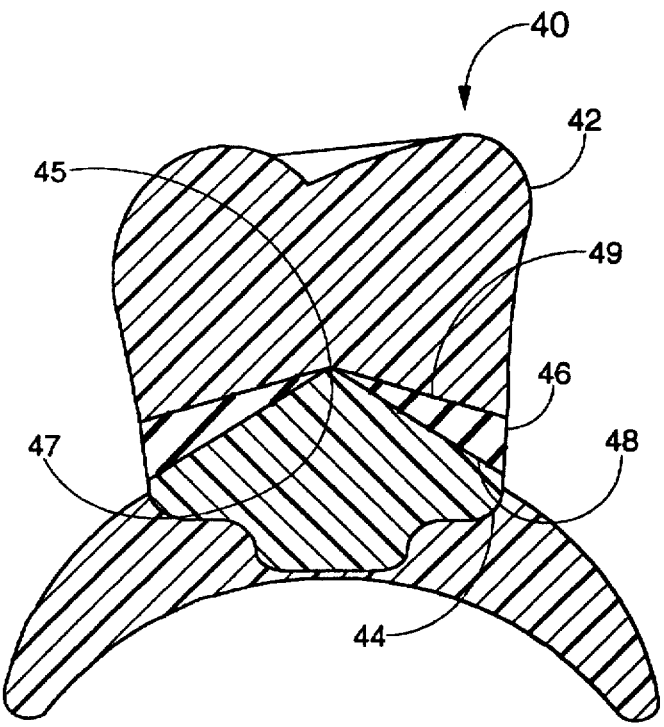
FIG. 3 shows a cross-sectional view of an alternate embodiment of the present invention.

FIG. 3 shows an alternative embodiment 40 of the invention, identical in every sense to the embodiment of FIG. 1 except that conical surfaces 48 and 49 are extended inwardly as planar contact areas 45 and 47 approach a point.

Figure 4:
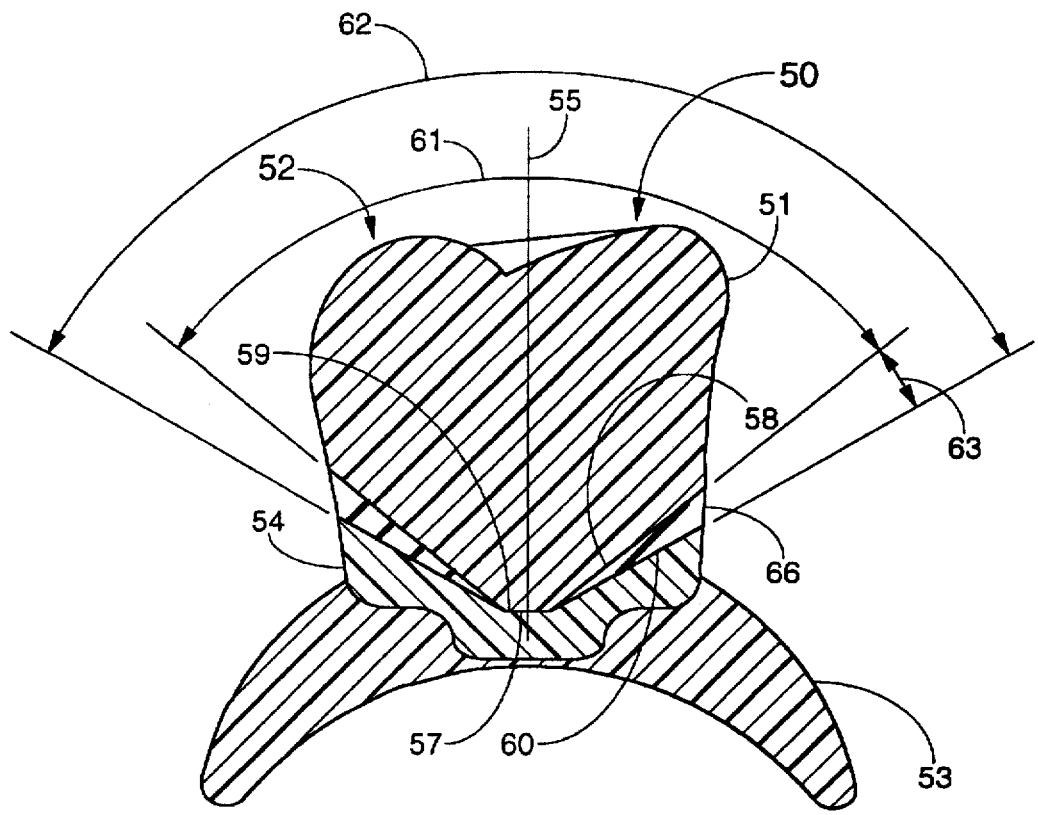
FIG. 4 shows a cross-sectional view of a second alternate embodiment of the present invention.

FIG. 4 shows a cross-section view of a second alternative embodiment of the invention. Vertical axis 55 is centrally located within the tooth side walls 51 and represents the normal line of action of biting forces imposed on crown 52. Base planar contact area 57 is located along central axis 55 and conical top surface 60 of base 54 extends from the perimeter of contact area 57 upwardly to the tooth side walls 51 at an included angle 62 of 130°. Crown planar contact area 59 abuts directly against base planar contact area 57 so that normal biting forces are carried along a hard, non-resilient load path. Conical crown surface 58 bounds crown contact area 59, overlying conical base surface 60 at an included angle 61 of 110°, and extends to tooth side walls 51 so that the surfaces diverge at the angle 63. Nesting of the edge of planar contact area 59 within the angle of conical base surface 60 resists lateral displacement forces while allowing flexibility for the crown 52 to realign in response to off-center biting forces. Conical surfaces 58 and 60 are bonded together by annular resilient intermediate portion 56. It is notable that, in this embodiment, a biting force on the crown 52 which is off-center to the left of central axis 55 and tends to displace crown 52 to the right, also tends to lift the right edge of base planar contact area 59 above the boundary line of conical base surface 60 so as to lessen resistance to rightward movement of crown 52. Thus, a steeper angle of conical surface 60, as compared to the embodiment of FIGS. 1 & 2, is required to resist lateral displacement.

It is to be understood that the present invention is not limited to the disclosed embodiments and may be expressed by rearrangement or modification or substitution of parts within the same spirit.

I claim:

1. A flexible artificial tooth comprising:

a relatively inelastic tooth base portion having generally vertical sides with an essentially vertical axis disposed centrally therewithin, a first planar area located on said vertical axis and normal thereto and a convex, substantially conical first surface bounding said first planar area and extending to said vertical sides, the inclination of said first surface relative to said vertical axis being in the range of 45° to 80°;

a relatively inelastic tooth crown portion including a second planar area in contact with, said first planar area and a concave, substantially conical second surface bounding said second planar area and overlying and diverging from said first surface so as to provide a wedge shaped annulus therebetween; and a substantially annular, relatively resilient intermediate portion bonded to said first and second diverging surfaces.

2. A flexible artificial tooth according to claim 1 wherein the area of said first planar area approaches a point.

3. A flexible artificial tooth according to claim 1 wherein the included angles of said conical surfaces are divergent by a difference of at least 6°.

4. A flexible artificial tooth according to claim 2 wherein the included angles of said conical surfaces diverge by a difference of at least 6°.

* * * * *